(12) United States Patent
Murakami et al.

(10) Patent No.: US 9,108,819 B2
(45) Date of Patent: Aug. 18, 2015

(54) FOLDING APPARATUS AND A FOLDING METHOD FOR A COMBINED BODY OF A CONTINUOUS SHEET RELATED TO AN ABSORBENT ARTICLE

(75) Inventors: Seiji Murakami, Kagawa (JP); Hirotomi Yamamoto, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 288 days.

(21) Appl. No.: 13/882,610

(22) PCT Filed: Oct. 25, 2011

(86) PCT No.: PCT/JP2011/074516
§ 371 (c)(1),
(2), (4) Date: Jul. 12, 2013

(87) PCT Pub. No.: WO2012/060249
PCT Pub. Date: May 10, 2012

(65) Prior Publication Data
US 2013/0296152 A1 Nov. 7, 2013

(30) Foreign Application Priority Data
Nov. 1, 2010 (JP) ................................. 2010-245277

(51) Int. Cl.
*B31F 1/08* (2006.01)
*B31F 1/10* (2006.01)
(Continued)

(52) U.S. Cl.
CPC .......... *B65H 45/00* (2013.01); *A61F 13/15747* (2013.01); *B65H 45/08* (2013.01); *B65H 2801/57* (2013.01)

(58) Field of Classification Search
CPC ..................... B31F 1/08; B31F 1/10

USPC .......................... 493/405, 416, 417, 423, 424
See application file for complete search history.

(56) References Cited

U.S. PATENT DOCUMENTS 5,800,329 A * 9/1998 Fager et al. ................... 493/417
5,868,727 A 2/1999 Barr et al.
(Continued)

FOREIGN PATENT DOCUMENTS

CN 1156678 A 8/1997
EP 1547561 A1 6/2005
(Continued)

OTHER PUBLICATIONS

Extended European Search Report issued Oct. 28, 2014, corresponding to European patent application No. 11837900.7.
(Continued)

*Primary Examiner* — Gloria R Weeks
(74) *Attorney, Agent, or Firm* — Lowe Hauptman & Ham, LLP

(57) ABSTRACT

A folding apparatus for a combined body of a continuous sheet includes a standing guide member disposed at a predetermined position in a conveying direction, and standing an one end section of the combined body in a width direction by bending a predetermined section of the combined body in the width direction and forming a bent section; a folding guide member corresponding to the stood one end section in the conveying direction for folding the stood one end section by laying the one end section towards a section located closer to another side than the one end section in the combined body; and a shift-regulating guide member for regulating shifting of the combined body towards the one side in the width direction by coming into contact, from the one side, with the combined body when laying the one end section towards the section located closer to the other side.

8 Claims, 8 Drawing Sheets

(51) Int. Cl.
*B65H 45/00* (2006.01)
*A61F 13/15* (2006.01)
*B65H 45/08* (2006.01)

(56) References Cited

U.S. PATENT DOCUMENTS

| | | | |
|---|---|---|---|
| 5,997,459 A * | 12/1999 | Kruger et al. | 493/441 |
| 6,234,229 B1 | 5/2001 | Tabuchi | |
| 6,371,901 B1 * | 4/2002 | Jackson et al. | 493/405 |
| 6,565,501 B1 * | 5/2003 | Trennepohl | 493/423 |
| 6,663,552 B1 * | 12/2003 | Yokoyama | 493/441 |
| 7,544,159 B2 * | 6/2009 | Petratto | 493/68 |
| RE45,256 E * | 11/2014 | Vogt et al. | 156/480 |
| 2012/0157283 A1 * | 6/2012 | Yamamoto | 493/394 |
| 2012/0157287 A1 * | 6/2012 | Yamamoto | 493/423 |
| 2012/0316047 A1 * | 12/2012 | Sablone et al. | 493/416 |
| 2013/0296152 A1 * | 11/2013 | Murakami et al. | 493/405 |

FOREIGN PATENT DOCUMENTS

| | | |
|---|---|---|
| JP | 53-035296 A | 4/1978 |
| JP | 3-226411 A | 10/1991 |
| JP | 9-000567 A | 1/1997 |
| JP | 9-215707 A | 8/1997 |
| JP | 2000-051272 A | 2/2000 |
| WO | 2005/087167 A1 | 9/2005 |
| WO | 2010/101283 A1 | 9/2010 |

OTHER PUBLICATIONS

Office Action dated Jan. 19, 2015, corresponding to Chinese patent application No. 201180061041.6.

International Search Report issued in PCT/JP2011/074516, dated Jan. 17, 2012, with English translation.

* cited by examiner

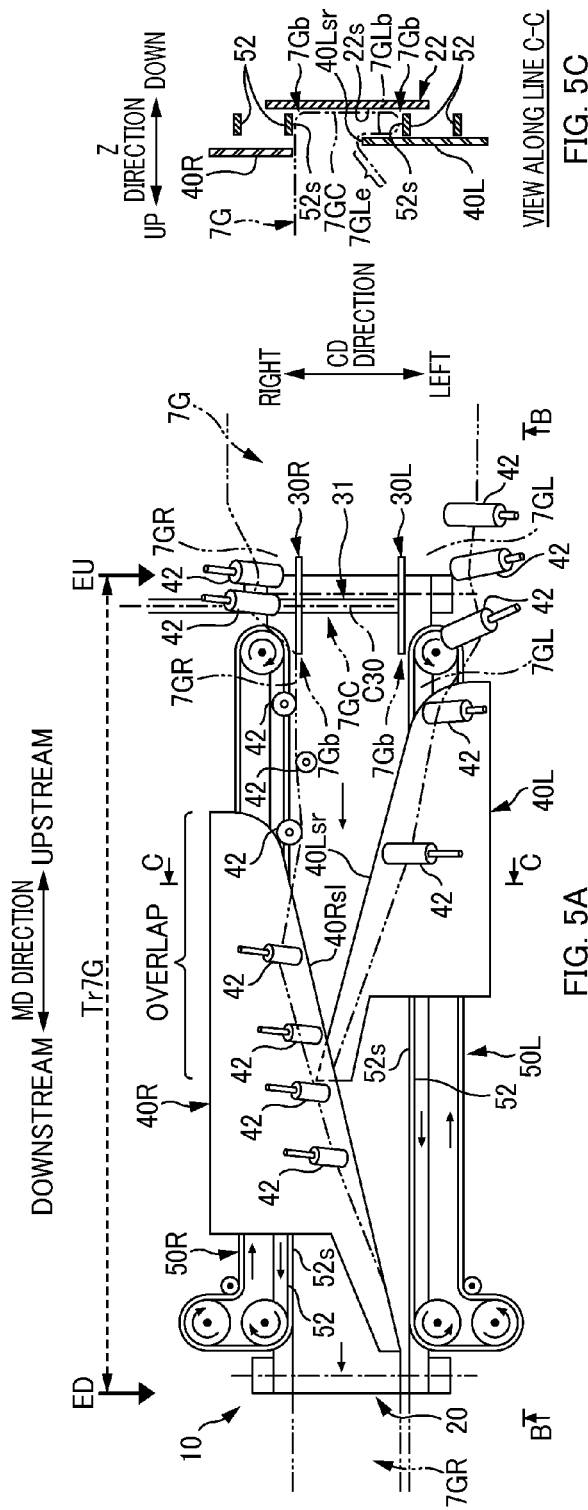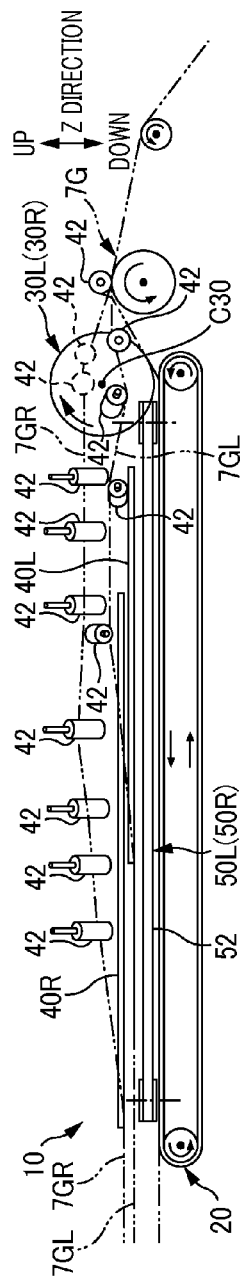
FIG. 5A
FIG. 5B VIEW ALONG LINE B-B
FIG. 5C VIEW ALONG LINE C-C

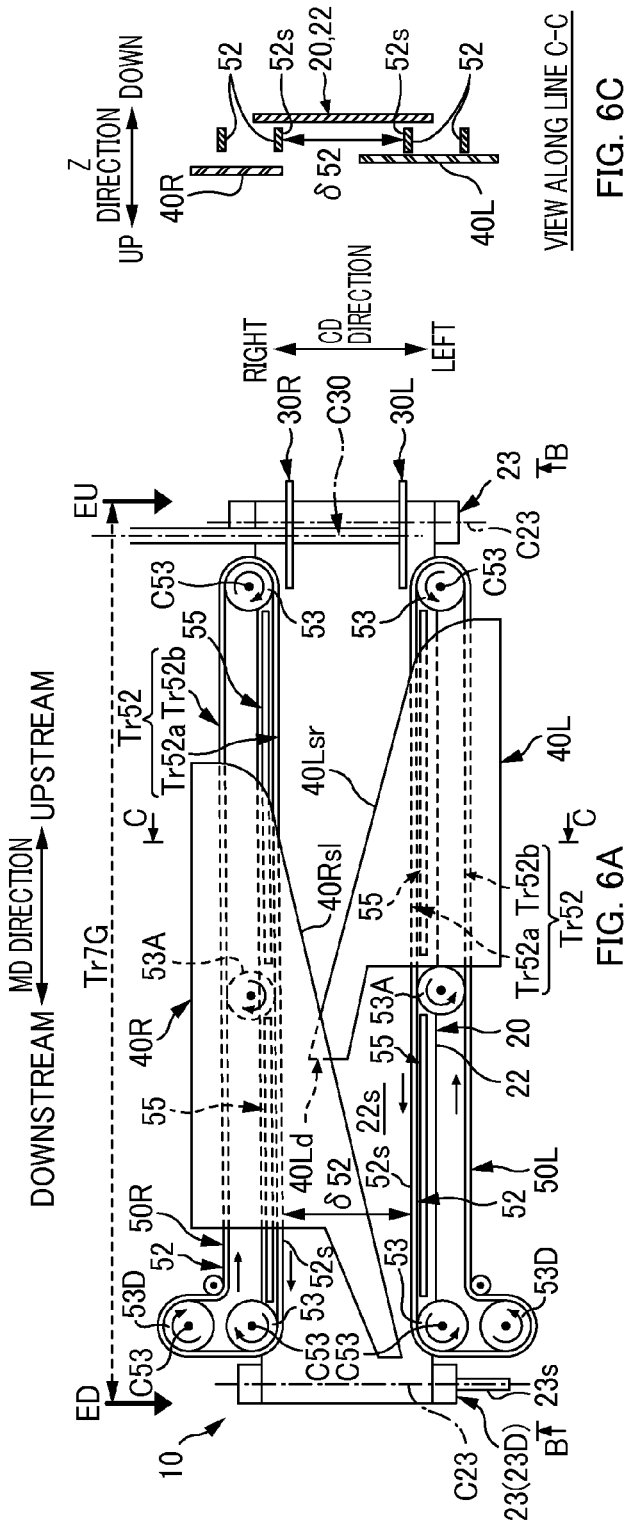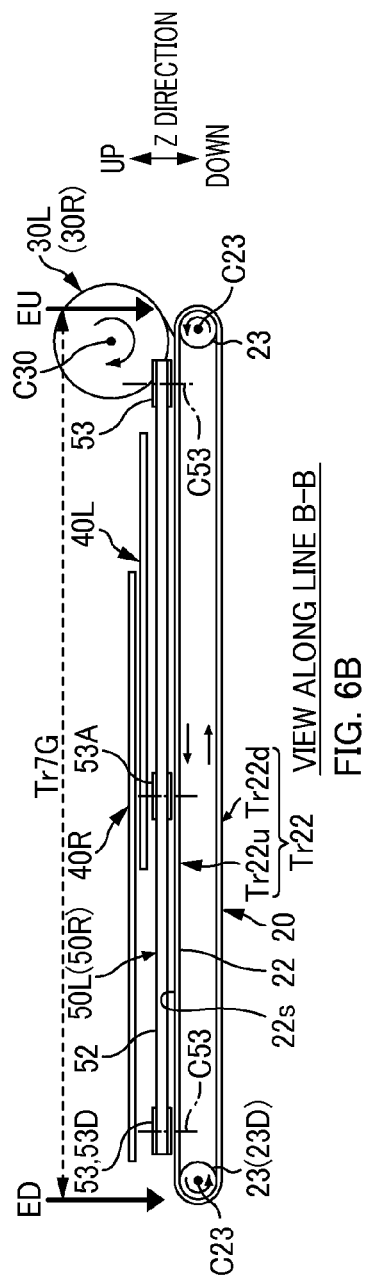

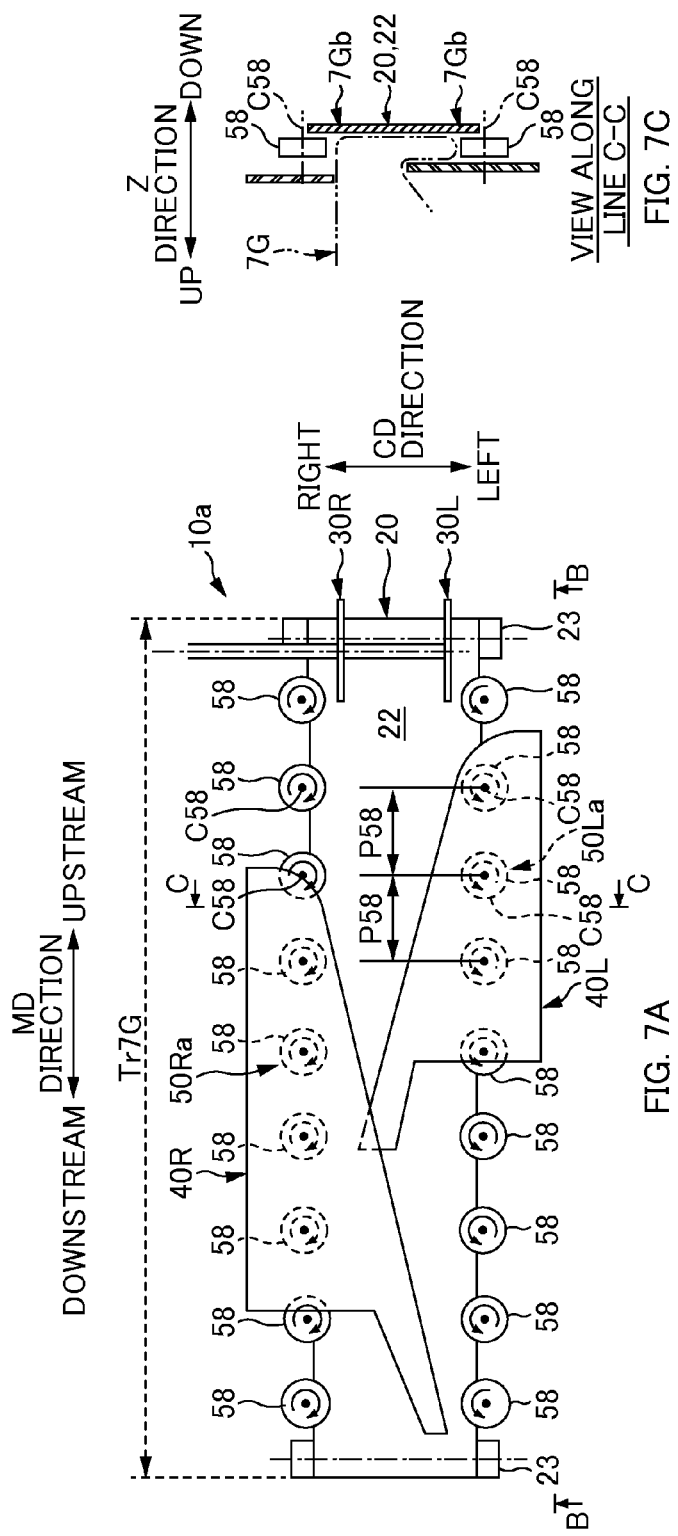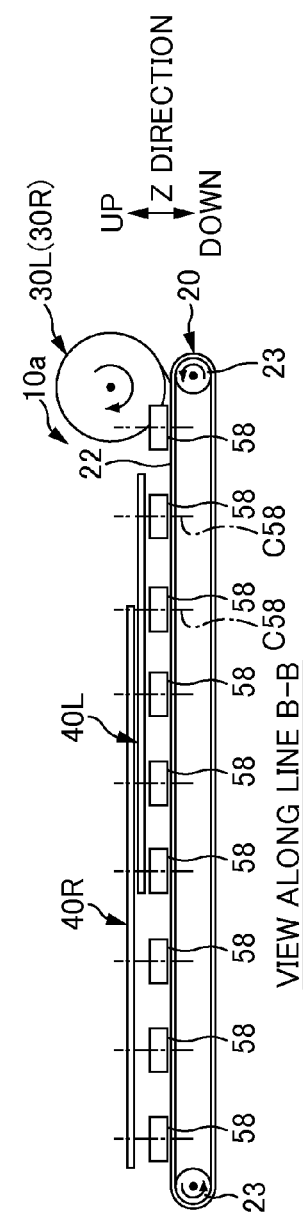

FOLDING APPARATUS AND A FOLDING METHOD FOR A COMBINED BODY OF A CONTINUOUS SHEET RELATED TO AN ABSORBENT ARTICLE

RELATED APPLICATIONS

The present application is a National Phase of PCT/JP2011/074516, filed Oct. 25, 2011, and is based on, and claims priority from, Japanese Application No. 2010-245277 filed Nov. 1, 2010.

TECHNICAL FIELD

The invention relates to a folding apparatus and a folding method for a combined body of a continuous sheet related to manufacturing of an absorbent article such as a sanitary napkin, a disposable diaper or the like.

BACKGROUND ART

In the final process of the conventional manufacturing line for the sanitary napkin, which is as an example of the absorbent article, the napkin which has been folded in three is packaged individually (PTL 1).

CITATION LIST

Patent Literature

[PTL 1]
Japanese Patent Application Laid-open Hei 3-226411

SUMMARY OF INVENTION

Technical Problem

This individual packaging of the napkin is performed, for example, as follow. FIGS. 1A to 1E are explanatory diagrams thereof. FIG. 1A is a schematic plan view showing the procedures of the individual packaging, and FIGS. 1B, 1C, 1D, and 1E are views in FIG. 1A, respectively taken along line B-B, line C-C, line D-D, and line E-E as viewed from the arrow side.

As shown in FIG. 1A, firstly, the continuous sheet 7 which is used for packaging is continuously conveyed by a suction belt conveyor 120 in the conveying direction, and a plurality of napkins 1, 1, . . . are placed thereon intermittently at a predetermined interval in that conveying direction. That is, these napkins 1, 1, . . . are moving in the conveying direction together with the continuous sheet 7 as a substantially unitary body.

On the other hand, at predetermined positions PL, PR in the conveying direction, a standing guide member 130 and a folding guide member 140 (not shown in FIG. 1A) are provided in order to fold in three together both of the continuous sheet 7 and the napkin 1.

Firstly, when passing a position at which the standing guide member 130 is provided, a section 7b of the continuous sheet 7 on one side in a width direction is bent as a bent section 7b by that guide member 130, as shown in FIG. 1B. Thereby, one end section 7L of the continuous sheet 7 in the width direction is stood together with one end section 1L of the napkin 1.

Next, as shown in FIGS. 1C and 1D, when passing the folding guide member 140, the folding guide member 140 lays the stood one end section 7L towards a substantially central section 7C of the continuous sheet 7, and thereby the one end section 7L is folded together with the one end section 1L of the napkin 1.

In order for the other end section 7R of the continuous sheet 7 to undergo that folding operation which consists of the standing step and the laying step, another standing guide member 130 and folding guide member 140, which are different from the foregoing ones, are provided for the other end section 7R at the predetermined position PR in the conveying direction (FIG. 1A). Therefore, after passing these guide members 130 and 140, the continuous sheet 7 and the napkin 1 are folded in three together as shown in FIG. 1E.

Thereafter, the napkin 1 which is three-folded together with the continuous sheet 7 passes a sealing apparatus, which is disposed downstream in the conveying direction and is not shown. When passing the sealing apparatus, a part 7p of the continuous sheet 7, which is between the adjacent napkins 1, 1 in the conveying direction, is sealed by heat-sealing or the like, as shown in FIG. 1A. That is, the part 7p is a part in which the napkin 1 does not exist in that sheet 7. Therefore, the continuous sheet 7, which is stuck in the thickness direction, is joined and integrated by welding or the like, and a sealed section 7j is formed. Thereafter, the continuous sheet 7 is divided into forward and after sections in the conveying direction at the position of the sealed section 7j by a suitable cutting device not shown in the figures; as a result the napkin 1 is packaged individually.

Incidentally, as shown in FIGS. 1C and 1D, a shift-regulating guide member 150, which regulates shifting of the continuous sheet 7 in the width direction, generally is provided together at the position at which the folding guide member 140 is provided. If the continuous sheet 7 shifts in the width direction when an end section 7L (7R) in the width direction is laid onto the substantially central section 7C, that shift-regulating guide member 150 regulates the shifting of the continuous sheet 7 by being in contact with the bent section 7b, etc of the continuous sheet 7, as shown in FIGS. 1C and 1D.

Herein, in the shift-regulating guide member 150, a fixed wall member 150, which is fixed immovably at the predetermined position in the width direction, is generally used and its wall 150w is along the conveying direction. Therefore, the continuous sheet 7 is conveyed while the bent section 7b etc of the continuous sheet 7 are sliding on that wall 150w. If the sliding resistance is large enough to stretch the continuous sheet 7 in the conveying direction, it is possible to cause positional shift in the following process in which the foregoing sealed section 7j is formed, or the like.

Further, depending on cases, the napkin 1 placed on the continuous sheet 7 is not fixed to the sheet, or is weakly fixed to the continuous sheet 7 in order to separate easily; that is, the napkin 1 is not fixed securely with adhesive etc. Further, those napkins 1, 1, . . . are arranged intermittently on the continuous sheet 7 in the conveying direction.

Therefore, when the bent section 7b etc of the continuous sheet 7 is sliding on the wall 150w of the fixed wall member 150, the downstream end 1bd of a bent section 1b of the napkin 1 in the conveying direction (FIG. 1A) may get stuck to the wall 150w with having the continuous sheet 7 in between the napkin and the wall, for example; this create a force to cease the conveying of the napkin 1 selectively. Therefore, it is possible that the napkin 1 is positioned on the continuous sheet 7 more upstream in the conveying direction than a correct position. In this case, a space between the napkins 1, 1 becomes narrower. Some of the foregoing sealed sections 7j, which is to be formed on the space, are formed on the napkins 1. Those napkins 1 becomes defective, which results in increase of fraction defective.

The invention has been made in view of the above problems, and an advantage thereof is to regulate the shifting of the continuous sheet by the shift-regulating guide member in the width direction and to reduce the sliding resistance which is caused between the continuous sheet and the shift-regulating guide member when folding together the one end section of the continuous sheet in the width direction and the one end section of an object of the napkin, etc.

Solution to Problem

An aspect of the invention to achieve the above advantage is
- a folding apparatus for a combined body of a continuous sheet related to an absorbent article, that folds at least one end section of the continuous sheet on one side in a width direction together with one end section of an object in the width direction while conveying the combined body in a conveying direction, the combined body being formed by placing intermittently a plurality of the objects on the continuous sheet at a predetermined interval, the conveying direction being a direction in which the continuous sheet continues, comprising:
- a standing guide member that is disposed at a predetermined position in the conveying direction, and that stands the one end section of the combined body in the width direction by bending a predetermined section of the combined body in the width direction and forming a bent section;
- a folding guide member that is disposed at a predetermined position in the conveying direction to correspond to the stood one end section and that folds the stood one end section by laying the one end section towards a section that is located closer to another side than the one end section in the combined body;
- a shift-regulating guide member that regulates shifting of the combined body towards the one side in the width direction by coming into contact, from the one side, with the combined body when laying the one end section towards the section that is located closer to the other side, wherein
- the shift-regulating guide member being either one of a roller member that rotates along the conveying direction and a belt member that moves along the conveying direction.

Further, a folding method for a combined body of a continuous sheet related to an absorbent article, that folds at least one end section of the continuous sheet on one side in a width direction together with one end section of an object in the width direction while conveying the combined body in a conveying direction, the combined body being formed by placing intermittently a plurality of the objects on the continuous sheet at a predetermined interval, the conveying direction being a direction in which the continuous sheet continues, comprising
- standing the one end section of the combined body in the width direction by bending a predetermined section of the combined body in the width direction and forming a bent section, using a standing guide member that is disposed at a predetermined position in the conveying direction;
- folding the stood one end section by laying the one end section towards a section that is located closer to another side than the one end section in the combined body, using a folding guide member that is disposed at a predetermined position in the conveying direction to correspond to the stood one end section; and
- regulating shifting of the combined body towards the one side in the width direction by bringing a shift-regulating guide member into contact, from the one side, with the combined body when laying the one end section towards the section that is located closer to the other side, wherein
- the shift-regulating guide member is either one of a roller member that rotates along the conveying direction and a belt member that moves along the conveying direction.

Other features of this invention will become apparent from the description in this specification and the attached drawings.

Advantageous Effects of Invention

According to the present invention, when folding both one end section in the width direction of the continuous sheet and one end section of an object such as a napkin, while regulating the movement in the width direction of the continuous sheet by the shift-regulating guide member, the sliding resistance between the continuous sheet and the shift-regulating guide member can be moderated.

BRIEF DESCRIPTION OF DRAWINGS

FIG. 3B is a front view of the napkin 1 packaged individually with the wrapping sheet 7a.

FIG. 5A is a schematic top view of the folding apparatus 10, FIG. 5B is a view taken along line B-B as viewed from the arrow side (side view) in FIG. 5A, and FIG. 5C is a view taken along line C-C as viewed from the arrow side in FIG. 5A.

FIGS. 6A to 6C are diagrams showing the case in which the combined body 7G and support rolls 42, 42, . . . are not shown respectively in FIGS. 5A to 5C.

FIG. 7A is a schematic top view of a folding apparatus 10a according to the second embodiment, FIG. 7B is a view taken along line B-B as viewed from the arrow side (side view) in FIG. 7A, and FIG. 7C is a view taken along line C-C as viewed from the arrow side in FIG. 7A.

DESCRIPTION OF EMBODIMENTS

Figure 1A:
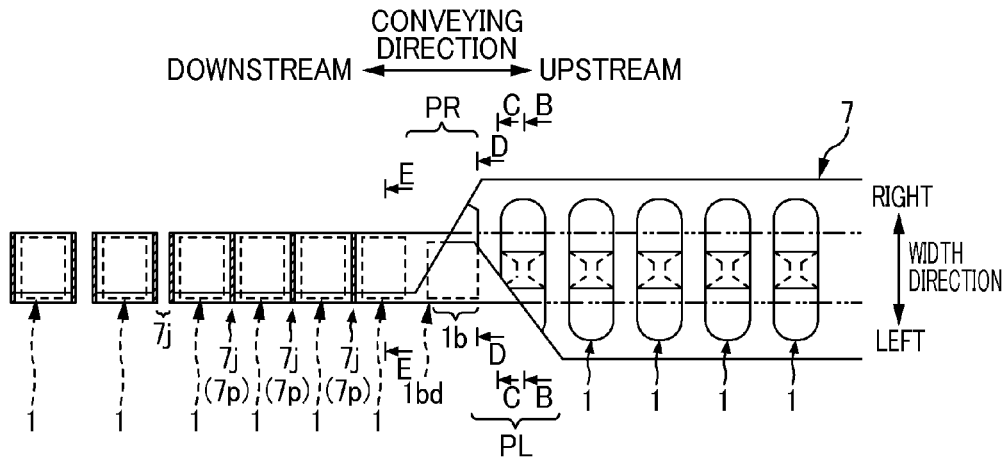
FIG. 1A is a schematic plan view showing the procedures of the individual packaging of the sanitary napkin 1.
Figure 1B:
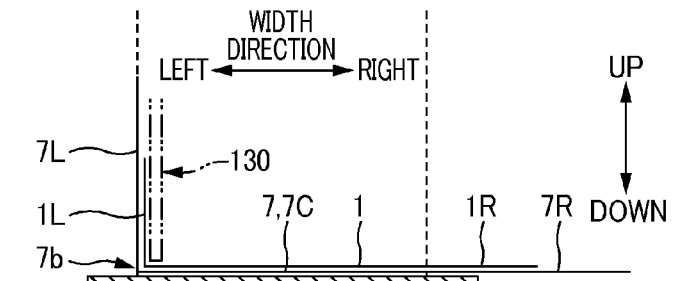
FIGS. 1B, 1C, 1D, and 1E are views in FIG. 1A, respectively taken along line B-B, line C-C, line D-D, and line E-E as viewed from the arrow side.
Figure 1C:
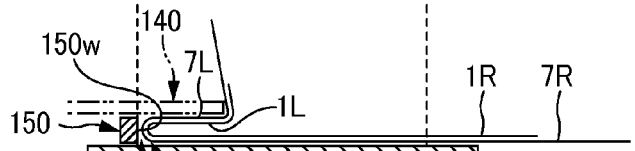
Figure 1D:
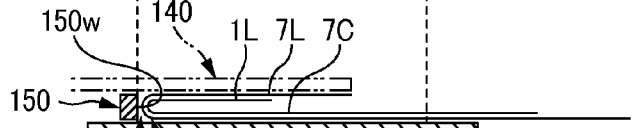
Figure 1E:
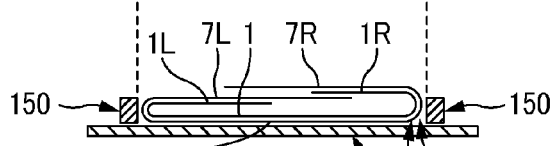

At least the following matters will be made clear by the description in the present specification and the accompanying drawings.

A folding apparatus for a combined body of a continuous sheet related to an absorbent article, that folds at least one end section of the continuous sheet on one side in a width direction together with one end section of an object in the width direction while conveying the combined body in a conveying direction, the combined body being formed by placing intermittently a plurality of the objects on the continuous sheet at a predetermined interval, the conveying direction being a direction in which the continuous sheet continues, comprising:

a standing guide member that is disposed at a predetermined position in the conveying direction, and that stands the one end section of the combined body in the width direction by bending a predetermined section of the combined body in the width direction and forming a bent section;

a folding guide member that is disposed at a predetermined position in the conveying direction to correspond to the stood one end section and that folds the stood one end section by laying the one end section towards a section that is located closer to another side than the one end section in the combined body;

a shift-regulating guide member that regulates shifting of the combined body towards the one side in the width direction by coming into contact, from the one side, with the combined body when laying the one end section towards the section that is located closer to the other side, wherein the shift-regulating guide member being either one of a roller member that rotates along the conveying direction and a belt member that moves along the conveying direction.

With such a folding apparatus for a combined body of a continuous sheet related to an absorbent article, the shift-regulating guide member is either the roller member that rotates or the belt member that moves. Therefore, the guide member can move along the conveying direction in synchronization with the conveying of the combined body. This can moderate sliding resistance between the guide member and the combined body which is being conveyed.

In such a folding apparatus for a combined body of a continuous sheet related to an absorbent article, desirably
the shift-regulating guide member is the belt member,
the belt member is an endless belt that moves along a predetermined path by obtaining from a power source a necessary force to move,
in a predetermined range of the path, the endless belt moves along the conveying direction in conjunction with the conveying of the combined body while a belt surface thereof is facing the bent section.

With such a folding apparatus for a combined body of a continuous sheet related to an absorbent article, the endless belt, which serves as the shift-regulating guide member, is not a driven belt which moves by obtaining the force to move from the combined body, but is a driving belt which moves along the path by obtaining the force to move from the power source. This can moderate effectively sliding resistance between the shift-regulating guide member which is the driving belt and the combined body which is being conveyed.

In such a folding apparatus for a combined body of a continuous sheet related to an absorbent article, desirably
the endless belt includes a plurality of suction holes on the belt surface, and
the belt surface sucks and holds the bent section by suction through the suction holes.

With such a folding apparatus for a combined body of a continuous sheet related to an absorbent article, while the bent section of the combined body is sucked and held by the belt surface of the endless belt, the endless belt moves along the conveying direction together with the combined body as a substantially unitary body. This can moderate effectively sliding resistance between the shift-regulating guide Member which is the endless belt and the combined body which is being conveyed.

In such a folding apparatus for a combined body of a continuous sheet related to an absorbent article, desirably
the folding apparatus further includes a conveying belt that includes a plurality of suction holes on a belt surface thereof and moves along the conveying direction, and
the combined body is conveyed by the conveying belt in the conveying direction while the belt surface is sucking and holding a central section of one surface of the continuous sheet by suction through the suction holes.

With such a folding apparatus for a combined body of a continuous sheet related to an absorbent article, the belt surface of the conveying belt sucks and holds the combined body to convey the same. Therefore, the combined body can be conveyed definitely.

In such a folding apparatus for a combined body of a continuous sheet related to an absorbent article, desirably
the shift-regulating guide member is the roller member,
the roller member is a drive roller that is driven and rotates about a predetermined rotational axis,
the drive roller is driven and rotates in conjunction with the conveying of the combined body while an outer peripheral face thereof is facing the bent section.

With such a folding apparatus for a combined body of a continuous sheet related to an absorbent article, the roller member, which serves as the shift-regulating guide member, is not a follower roller which rotates by obtaining the rotating force from the combined body, but is a drive roller which rotates by obtaining the rotating force from the power source. This can moderate sliding resistance between the shift-regulating guide member which is the drive roller and the combined body which is being conveyed.

In such a folding apparatus for a combined body of a continuous sheet related to an absorbent article, desirably
a plurality of the roller members are arranged at a predetermined arrangement interval in the conveying direction, and
the arrangement interval is smaller than the predetermined interval related to the objects.

With such a folding apparatus for a combined body of a continuous sheet related to an absorbent article, the arrangement interval of the roller members is smaller than the predetermined interval of the object. This enables the object to smoothly transfer along the conveying direction from the roller member to the next roller member.

In such a folding apparatus for a combined body of a continuous sheet related to an absorbent article, desirably
the standing guide members are disposed on respectively both end sections of the combined body in the width direction to correspond respectively to the both end sections,
the folding guide members are disposed on respectively both end sections of the combined body in the width direction to correspond respectively to the both end sections, and
the shift-regulating guide members are disposed on respectively both end sections of the combined body in the width direction to correspond respectively to the both end sections.

With such a folding apparatus for a combined body of a continuous sheet related to an absorbent article, the standing guide member and folding guide member are provided on the both sides of the combined body in the width direction. Therefore, the combined body can be folded in three in the width direction.

Further, the shift-regulating guide member are provided on the both sides of the combined body in the width direction. This can moderate sliding resistance which may be caused between the combined body and the shift-regulating guide member when folding in three.

Further, a folding method for a combined body of a continuous sheet related to an absorbent article, that folds at least one end section of the continuous sheet on one side in a width direction together with one end section of an object in the width direction while conveying the combined body in a conveying direction, the combined body being formed by placing intermittently a plurality of the objects on the continuous sheet at a predetermined interval, the conveying direction being a direction in which the continuous sheet continues, comprising:

standing the one end section of the combined body in the width direction by bending a predetermined section of the combined body in the width direction and forming a bent section, using a standing guide member that is disposed at a predetermined position in the conveying direction;

folding the stood one end section by laying the one end section towards a section that is located closer to another side than the one end section in the combined body, using a folding guide member that is disposed at a predetermined position in the conveying direction to correspond to the stood one end section; and regulating shifting of the combined body towards the one side in the width direction by bringing a shift-regulating guide member into contact, from the one side, with the combined body when laying the one end section towards the section that is located closer to the other side, wherein the shift-regulating guide member is either one of a roller member that rotates along the conveying direction and a belt member that moves along the conveying direction.

With such a folding method for a combined body of a continuous sheet related to an absorbent article, the shift-regulating guide member is either the roller member that rotates or the belt member that moves. Therefore, the guide member can move along the conveying direction in conjunction with the conveying of the combined body. This can moderate sliding resistance between the guide member and the combined body which is being conveyed.

First Embodiment

The folding apparatus 10 according to the first embodiment is used in the manufacturing line of the sanitary napkin 1, which is as an example of the absorbent article.

Figure 2A:
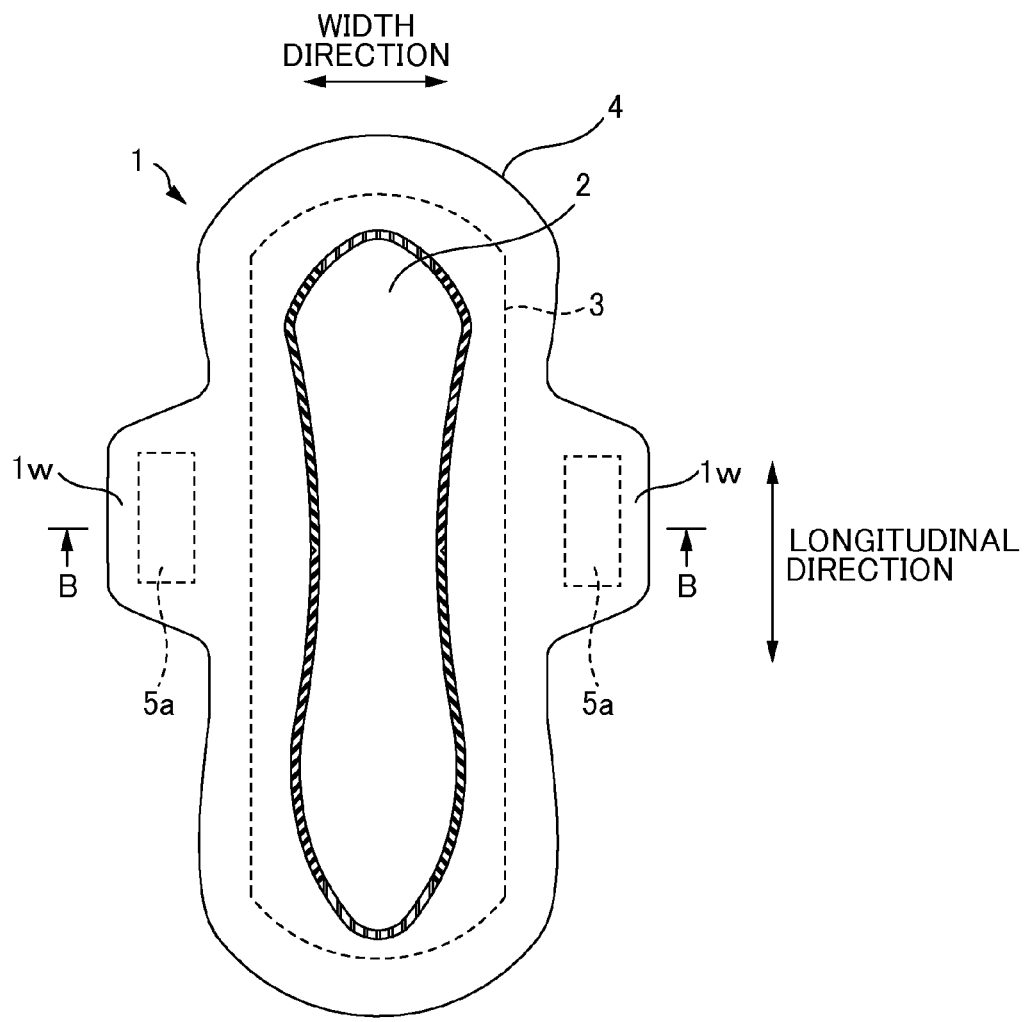
FIG. 2A is a plan view of the napkin 1.
Figure 2B:
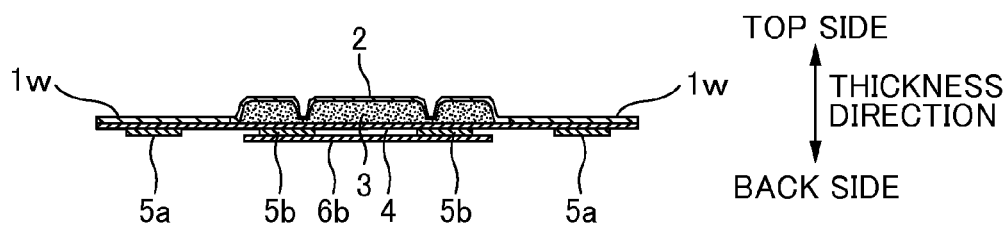
FIG. 2B is a cross-sectional view taken along line B-B in FIG. 2A.
Figure 3A:
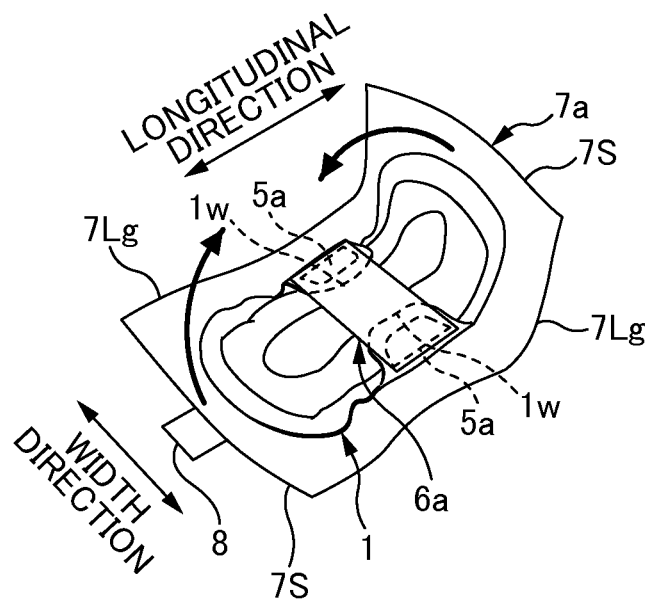
FIG. 3A is a perspective view of a wrapping sheet 7a and the napkin 1.
Figure 3B:
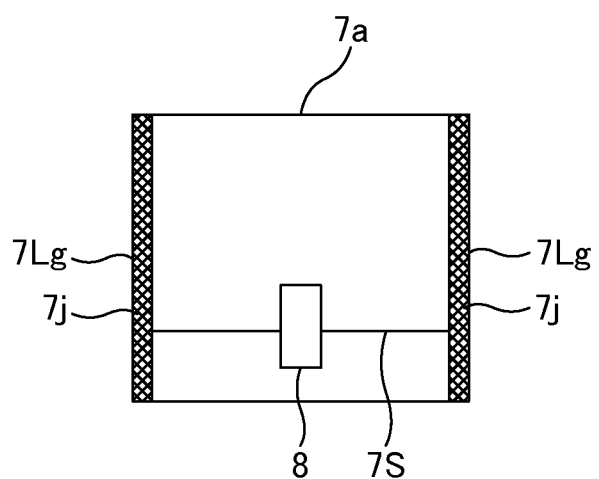

FIG. 2A is a plan view of the napkin 1 and FIG. 2B is a cross-sectional view taken along line B-B in FIG. 2A. Further, FIG. 3A is a perspective view of the wrapping sheet 7a and the napkin 1, and FIG. 3B is a front view of the napkin 1 packaged individually with the wrapping sheet 7a.

The napkin 1 includes, for example, a liquid-permeable top sheet 2 such as nonwoven fabric etc, a liquid-impermeable back sheet 4 such as film etc, and an absorbent body 3 which is sandwiched between these two sheets and absorbs bodily fluid. These sheets 2 and 4 are stuck together by the section extending beyond the absorbent body 3; thereby the absorbent body 3 is held between these sheets 2 and 4.

The planer shape of the napkin 1 is a substantially rectangular shape having a longitudinal direction and the width direction. However, depending on cases, a pair of wings $1w$ and $1w$ extending outwardly in the width direction may be included substantially in the longitudinal center of the napkin 1, as this example.

In using the napkin 1, these wings $1w$ and $1w$ are folded towards the back sheet 4 side, and adhere and are fixed to an undergarment to sandwich the undergarment together with the back sheet 4. Therefore, adhesives 5a and 5a are applied to surfaces which are to come into contact with the undergarment when the wings $1w$ and $1w$ are folded. Further, adhesives 5b and 5b to be used for the same purpose are also applied to surfaces of the back sheet 4, which are to come into contact with the undergarment in using the napkin 1.

As shown in FIGS. 2B and 3A, for the purpose of keeping adhesion of the adhesives 5a and 5b until the napkin 1 is used, protection sheets 6a and 6b are provided in the area to which the foregoing adhesives 5a and 5b are applied, and the sheets 6a and 6b cover the applied area. More specifically, before the use, the pair of wings $1w$ and $1w$ are folded respectively onto the top sheet 2, and the single protection sheet 6a covers the wings $1w$ and $1w$, which protects the adhesives 5a and 5a on the wings $1w$ and $1w$ (FIG. 3A). On the other hand, in the applied area of the adhesives 5b and 5b in the back sheet 4, the protection sheet 6b covering a substantially entire surface of the area is also provided, which protects the adhesives 5b and 5b (FIG. 2B).

Further, before the use, as shown in FIG. 3B, the napkin 1 is packaged individually with the wrapping sheet 7a such as nonwoven fabric, etc. That is, as shown in FIG. 3A, the state is as follows: the wrapping sheet 7a has a substantially rectangular shape of a single sheet and is larger in planer size than the napkin 1; the napkin 1 is placed on that wrapping sheet 7a and is three-folded in the longitudinal direction together with the wrapping sheet 7a, with their longitudinal direction in the same direction. Further, a short edge 7S of the wrapping sheet 7a, which is three-folded as shown in FIG. 3B, is fixed to that wrapping sheet 7a with tape 8. In a pair of long edges 7Lg of the wrapping sheet 7a, the edges which are opposite to each other are welded or adhere, and this results in forming the sealed section 7j. In this regards, when the napkin 1 is being placed as mentioned above, the protection sheet 6b of the napkin 1 may adhere and be fixed to the wrapping sheet 7a at a plurality of positions; in this example, the protection sheet 6b of the napkin 1 adheres to the wrapping sheet 7a at three longitudinal positions.

Figure 4:
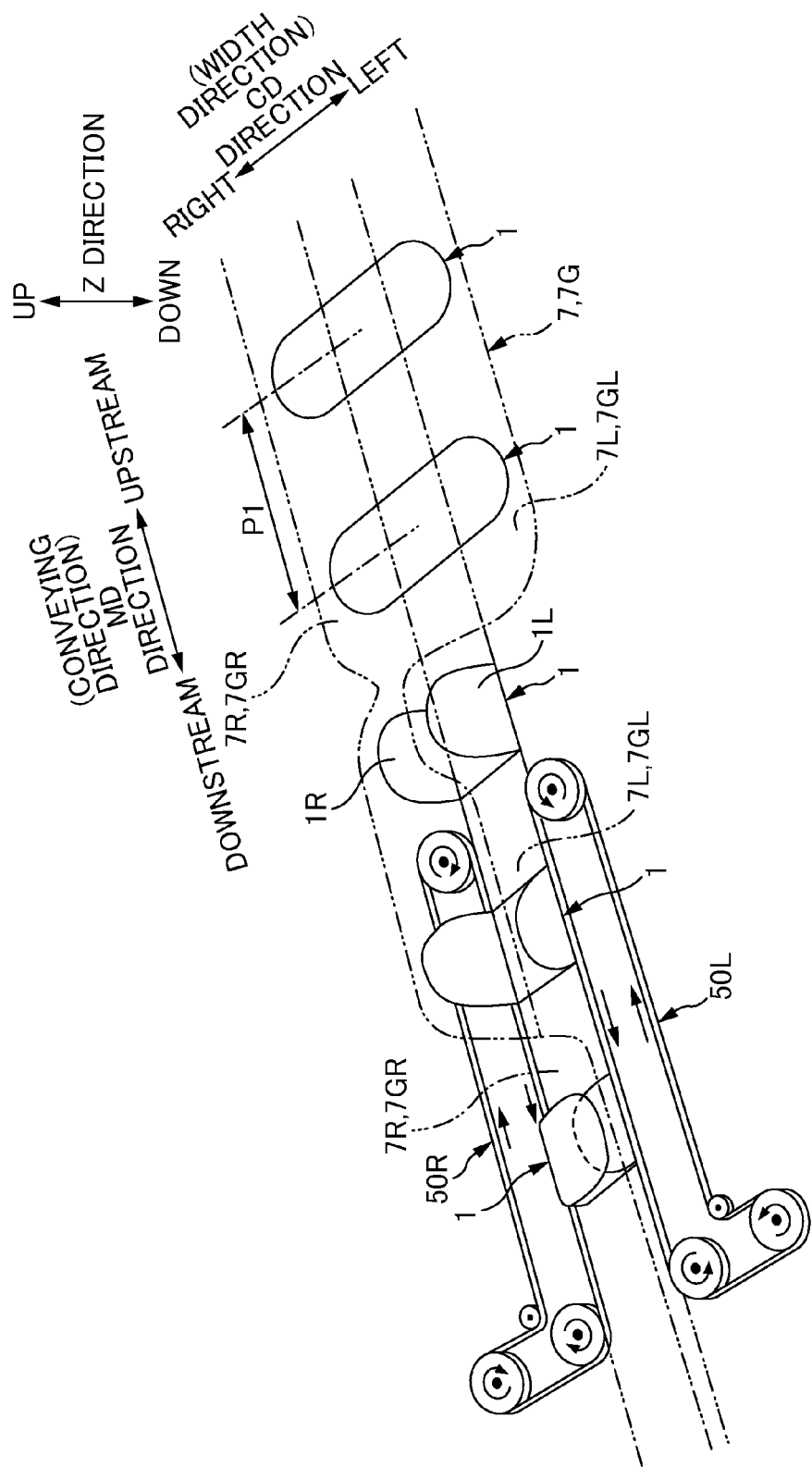
FIG. 4 is a schematic perspective view showing how a folding apparatus 10 according to the first embodiment folds a combined body 7G.

FIGS. 4 to 6C are explanatory diagrams of the folding apparatus 10 which folds in three the napkin 1 together with the wrapping sheet 7a. FIG. 4 is schematic perspective view showing how the folding apparatus 10 folds the combined body 7G, FIG. 5A is a schematic top view of the folding apparatus 10, FIG. 5B is a view taken along line B-B as viewed from the arrow side in FIG. 5A (side view), and FIG. 5C is a view taken along line C-C as viewed from the arrow side in FIG. 5A. Further, FIGS. 6A to 6C are diagrams showing the case in which the combined body 7G and support rolls 42, 42, . . . are not shown respectively in FIGS. 5A to 5C.

That folding apparatus 10 is generally provided in the final process of the manufacturing line for the napkin 1. Therefore, when being conveyed to that folding apparatus 10, the napkin 1 itself has been finished; that is, the wings $1w$ and $1w$ of the napkin 1 are folded and the foregoing protection sheets 6a and 6b has been provided, as shown in FIG. 3A. On the other hand, the wrapping sheet 7a is, as shown in FIG. 4, in the form of the continuous sheet 7 which continues along the predetermined conveying direction. on the upper surface which is one surface of the continuous sheet 7, the plurality of napkins 1, 1, . . . (corresponding to objects) which are finished as mentioned above are placed intermittently at predetermined intervals in the conveying direction. In this regards, each of these napkins 1, 1, . . . may be weakly fixed to the continuous sheet 7 with adhesive, etc, as mentioned above.

Further, at this stage, each of the napkins 1 is placed whose longitudinal direction is along the width direction of the continuous sheet 7, as shown in FIG. 4. Therefore, by folding in three the continuous sheet 7 in the width direction of the continuous sheet 7, the napkin 1 is folded in three together with the continuous sheet 7. That is, as shown in FIG. 4, while being conveyed by the folding apparatus 10 in the conveying direction, the one end section 7L of the continuous sheet 7 in the width direction is folded, and the other end section 7R is also folded; as a result, the continuous sheet 7 and the napkin 1 are folded in three.

The folding apparatus 10 will be described below. In the description, the continuous sheet 7 of the wrapping sheet 7a is merely referred to as the "continuous sheet 7". Further, the unitary body which consists of the continuous sheet 7 and the napkin 1 placed thereon is merely referred to as "combined body 7G of continuous sheet 7" or "combined body 7G". Furthermore, the conveying direction in which the continuous sheet 7 continues is referred to as the "MD direction", and the width direction of the continuous sheet 7 is referred to as the "CD direction" or "left-to-right direction". A direction perpendicular to both of these MD direction and CD direction is referred to as the "Z direction". In this regards, that Z direction is along the same direction as the thickness direction of the combined body 7G or the continuous sheet 7, and is along the up-and-down direction in this example. Further, the Z direction, the MD direction, and the CD direction are perpendicular to one another.

As shown in FIGS. 5A to 5C, the folding apparatus 10 includes: a suction belt conveyor 20 which is for conveying the combined body 7G which is formed by placing the napkin 1 on the continuous sheet 7; a pair of left and right standing guide members 30L and 30R which are for standing each of end sections 7GL and 7GR of that combined body 7G in the CD direction in order to start the folding; a pair of left and right folding guide members 40L and 40R which are for laying and folding each of the stood end sections 7GL and 7GR on the central section 7GC in the CD direction; and a pair of left and right shift-regulating guide members 50L and 50R which are for stabilizing a position at which the combined body 7G is located in the CD direction when folding. In this regards, the foregoing end sections 7GL and 7GR correspond to "one end section of combined body in the width direction" according to the claims, and the foregoing central section 7GC corresponds to the "section that is located closer to another side than the one end section".

As shown in FIGS. 6A to 6C, the suction belt conveyor 20 includes an endless belt 22 (corresponding to belt member). The endless belt 22 is wrapped around a pair of rollers 23 and 23 which are arranged spaced in the MD direction. At least either one of the pair of rollers 23 and 23 is a drive roller 23D which is driven and rotated by a suitable not shown power source such as an electric motor, etc. Therefore, as shown in FIG. 6B, the endless belt 22 moves along a path Tr22, which is a substantially elliptical path elongated in the MD direction. An upper straight path Tr22u of the path Tr22 is used as a conveying path Tr7G which is for conveying the combined body 7G, and a lower straight path Tr22d is used as a return path in which the region of the endless belt 22 returns to the upstream end EU when it reaches the downstream end ED of the conveying path Tr7G. In this regards, a belt surface 22s of the endless belt 22 is parallel to the CD direction because the rotational axes C23 of the foregoing pair of rollers 23 and 23 are each along the CD direction.

On the belt surface 22s of the endless belt 22, a plurality of suction holes (not shown) are formed. Suction through these suction holes generate suction force on the belt surface 22s. The endless belt 22 moves along the path Tr22 while the belt surface 22s is sucking and holding a lower surface of the continuous sheet 7 of the combined body 7G. As a result, the combined body 7G is conveyed from upstream to downstream in the MD direction along the upper straight path Tr22u, which is the foregoing conveying path Tr7G.

The pair of left and right standing guide members 30L and 30R are each arranged at the upstream end EU of the conveying path Tr7G of the suction belt conveyor 20 or at a position more upstream than the upstream end EU; in the example of FIGS. 6A and 6B, the guide members 30L and 30R are arranged at the upstream end EU. Further, the standing guide members 30L and 30R are arranged above the combined body 7G. Furthermore, each of the standing guide members 30L and 30R is a plate member having a perfect circular shape and rotates about a rotational axis C30 which is along the CD direction; the standing guide members 30L and 30R are arranged lined up in the CD direction. The outer edges of the pair of circular plate members 30L and 30R are, from above, in contact with two sections of the combined body 7G in the CD direction, as shown in FIGS. 6A and 6B. Therefore, these two sections or neighbouring portion thereof function as the bent sections 7Gb and 7Gb. The end sections 7GL and 7GR in the CD direction are bent upwardly. As a result, each of the left and right end sections 7GL and 7GR of the combined body 7G are stood upwardly.

Herein, the pair of circular plate members 30L and 30R are the same in external diameter, for example; further, both of the circular plate members 30L and 30R are coaxially fixed to and supported by a shaft member 31, which rotates about the rotational axis C30 extending along the CD direction. Therefore, both of the circular plate members 30L and 30R rotates together with the shaft member 31 as a unitary body. Further, that shaft member 31 is driven and rotates by transmitting power, for example, from a power source of the foregoing suction belt conveyor 20 through a suitable power-transmitting member (not shown) such as a pulley, a timing belt, etc. Furthermore, for example, the rate of rotation of the power-transmitting member, etc are set such that the circumferential speed of the outer edges of the circular plate members 30L and 30R is the same as the conveying speed of the combined body 7G.

This effectively prevents a phenomenon which occur if the relative speed difference is great, such as a phenomenon that the circular plate members 30L and 30R excessively pull the combined body 7G in the MD direction. As a result, each of the circular plate members 30L and 30R can smoothly form the starting point of the standing section on the combined body 7G; the bent sections 7Gb and 7Gb can be formed stably.

It should be noted that a power source only for driving these circular plate members 30L and 30R may be provided; that is, these circular plate members 30L and 30R may be driven differently from the suction belt conveyor 20. In this case, the foregoing power source may be controlled by a suitable controller in synchronization with the conveying of the combined body 7G such that the circumferential speed of the circular plate members 30L and 30R changes together with the conveying speed of the combined body 7G. Further, each of the circular plate members 30L and 30R may be configured to be an unpowered circular plate which gets turned by obtaining the rotating force from the contact with the combined body 7G. In this case, the speed of a portion of the circular plate members 30L and 30R which is contact with the combined body 7G can be adjusted to match subttle changes to the speed of the combined body 7G.

Furthermore, instead of the foregoing circular plate members 30L and 30R, a single roll member (not shown) may be used as the standing guide member 30L and 30R. This roll member is also coaxially with the shaft member 31 and is fixed to and supported by the shaft member 31. The shaft member 31 rotates about the rotational axis which is along the CD direction. Further, an outer peripheral face of the roll member is to be in contact with the combined body 7G, and the length of the peripheral face in the CD direction is set to the substantially same length as the space between a pair of the bent sections 7Gb and 7Gb of the combined body 7G. In this case, the edges of the outer peripheral face of the roll member comes into contact with portions of the combined body 7G. Those portions or neighbouring portions thereof serve as the bent sections 7Gb and 7Gb, and are bent. As a result, the end sections 7GL and 7GR of the combined body 7G in the CD direction are stood.

The pair of left and right folding guide members 40L and 40R, as mentioned above, have a function to fold in three the combined body 7G as follows. The left and right end sections 7GL and 7GR of the combined body 7G are stood by the standing guide member 30L and 30R. The folding guide members 40L and 40R lay and fold each of the end sections 7GL and 7GR from above onto the combined body 7G. The folding guide members 40L and 40R having the foregoing function are located respectively at positions which are downstream from the standing guide members 30L and 30R in the conveying path Tr7G; and, the folding guide members 40L and 40R are on the both left and right sides, as shown in FIGS. 6A and 6B. It should be noted that the folding guide member 40L which is arranged left in the CD direction is hereinafter referred to as the "left guide member 40L" and the folding guide member 40R which is arranged right as the "right guide member 40R". In the course of movement of the combined body 7G downstream along the conveying path Tr7G, when passing the position at which the left guide member 40L is provided, the stood left end section 7GL is laid by the left guide member 40L. On the other hand, when passing the position at which the right guide member 40R is provided, the stood right end section 7GR is laid by the right guide member 40R.

Specifically speaking, the left guide member 40L is a flat plate member 40L which is arranged, above the conveying path Tr7G, parallel to the belt surface 22s of the endless belt 22 of the suction belt conveyor 20. The left guide member 40L is opposite to the belt surface 22s, having a slightly larger space between itself and the belt surface 22s than the thickness of the three-folded combined body 7G. Further, as shown in FIG. 6A, the planer shape of the flat plate member 40L is substantially a triangle including a plurality of edges; the edge 40Lsr (hereinafter referred to as the right edge 40Lsr) which is located over the combined body 7G gradually extends to the right as it nears the downstream end in the MD direction.

In this configuration, in the left end section 7GL of the combined body 7G, a portion 7GLe, which is located closer to the standing side than the position being in contact with the right edge 40Lsr of the left guide member 40L, remains upright, as shown in FIG. 5C. On the other hand, a portion 7GLb, which is located closer to the bent section 7Gb than the contact position with the right edge 40Lsr, slides in between the lower surface of the left guide member 40L and the belt surface 22s. Thereby, the portion 7GLb is laid.

Therefore, with the foregoing left guide member 40L, the position of the stood left end section 7GL at which the end section 7GL is in contact with the right edge 40Lsr gradually moves right as the combined body 7G moves downstream (FIG. 5A). Therefore, the laid portion of the left end section 7GL becomes gradually wider from left to right. As a result, the whole of the left end section 7GL is laid finally.

In the same manner, as shown in FIGS. 6A and 6B, the right guide member 40R is a flat plate member 40R which is arranged, above the conveying path Tr7G, parallel to the belt surface 22s of the endless belt 22, The right guide member 40R is installed slightly above the left guide member 40L. This is because the right guide member 40R and the left guide member 40L overlap in their planary positions in the downstream end 40Ld of the left guide member 40L when viewed from above. Further, the planer shape of the flat plate member 40R is a substantially triangle including a plurality of edges; the edge 40Rs1 which is located over the combined body 7G (hereinafter referred to as the left edge 40Rs1) gradually extends to the left as it nears the downstream end in the MD direction.

Therefore, in the stood right end section 7GR, a position at which the section 7GR is in contact with the left edge 40Rs1 of the right guide member 40R gradually moves left as the combined body 7G moves downstream (FIG. 5A). Therefore, the laid portion of the right end section 7GR becomes gradually wider from left to right. As a result, the whole of the right end section 7GR is laid finally.

The left guide member 40L and the right guide member 40R are arranged in the MD direction so that their positions do not match, as shown in FIG. 5A. In other words, the left guide member 40L is located upstream than the right guide member 40R, and the left guide member 40L and the right guide member 40R are arranged overlapping each other along the MD direction.

Therefore, the combined body 7G, which is being conveyed, starts to pass the left guide member 40L; while passing the left guide member 40L, the combined body 7G starts to pass the right guide member 40R. At a time when the combined body 7G has finished passing the left guide member 40L, the body 7G is still passing the right guide member 40R, and thereafter finishes passing the right guide member 40R. Thus, the laying action for the left end section 7GL of the combined body 7G starts and ends prior to the right end section 7GR. Therefore, the right end section 7GR covers the left end section 7GL which has been laid prior thereto on the central section 7GC of the combined body 7G. As a result, the combined body 7G is folded in three.

Figure 8:
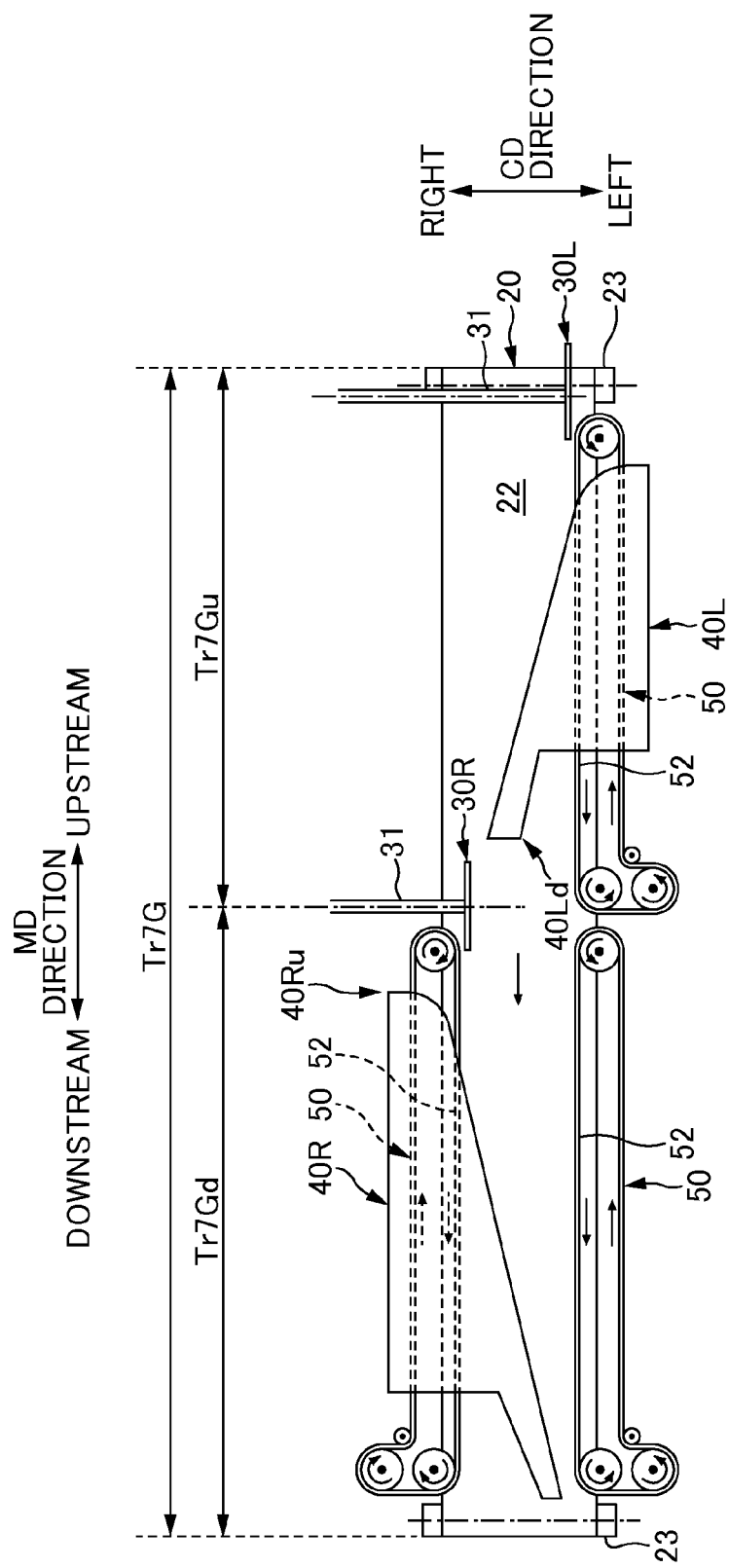
FIG. 8 is a schematic top view in the configuration in which a left guide member 50L and a right guide member 50R do not overlap each other.

However, the guide members 40L and 40R do not have to overlap along the MD direction. That is, as shown in FIG. 8 to be described later, an upstream end 40Ru of the right guide member 40R may be located downstream in the MD direction than a downstream end 40Ld of the left guide member 40L. The left and right guide members 40L and 40R put a load such as a force to stretch the combined body 7G when folding the combined body 7G; the foregoing configuration enable the load to be distributed upstream and downstream in the conveying direction and to reduce. Therefore, in terms of reducing the load, this configuration is more desirable. However, the overlapping configuration shown in the foregoing FIG. 5A can shorten the total length of the folding apparatus 10 itself along the MD direction. Therefore, in terms of making the folding apparatus smaller, the first embodiment is more preferable. The unoverlapping configuration in FIG. 8 will be described later in detail.

Further, as shown in FIGS. 5A and 5B, it is preferable that portions of the end sections 7GL and 7GR of the combined body 7G, which are located closer to the standing side, are tense in the CD direction by the following means. A plurality of support rolls 42, 42, ..., which are respectively moved and rotated, are arranged in the vicinity of the right edge 40Lsr of the left guide member 40L or the left edge 40Rs1 of the right guide member 40R. And, the outer peripheral faces of these support rolls 42, 42, ... are brought into contact with the portions. Thereby, a tensile force in the CD direction is exerted on the portions. With such a configuration, the portions are laid by the guide members 40L and 40R corresponding thereto while being tense in the CD direction. This can effectively prevent the occurrence of creases during the laying action.

The pair of left and right shift-regulating guide members 50L and 50R are arranged, as shown in FIG. 5A, along the MD direction at positions on the both sides of the conveying path Tr7G of the suction belt conveyor 20 (that is, on the both left and right sides in the CD direction). When laying each of the end sections 7GL and 7GR of the combined body 7G, the guide members 50L and 50R respectively regulate shifting of the combined body 7G in the CD direction by being in contact with the bent section 7Gb of the combined body 7G or neighbouring portion thereof, etc. This stabilizes position of that combined body 7G in the CD direction.

It should be noted that the shift-regulating guide members 50L and 50R, which are provided at the positions on the both left and right sides, are arranged substantially symmetrically with respect to the MD direction, and the other points are almost the same. Therefore, in the following description, the left shift-regulating guide member 50L will be selected to be described and the description is applied to the right shift-regulating guide member 50R.

The main body of the shift-regulating guide member 50L is an endless belt 52 such as a rubber belt etc, as shown in FIGS. 6A and 6B. The endless belt 52 is wrapped around a pair of pulleys 53 and 53 which are respectively arranged on the downstream end ED and the upstream end EU in the conveying path Tr7G. Further, a drive pulley 53D, which is driven and rotated by a suitable power source, is provided in the vicinity of at least either one of the pair of pulleys 53 and 53. The endless belt 52 is also wrapped around the drive pulley 53D. Therefore, the endless belt 52 is driven and moves along the path Tr52, which is a substantially elliptical path elongated in the MD direction. It should be noted that, in this example, the path Tr52 includes a straight path Tr52a inside in the CD direction (hereinafter referred to as the inside straight path Tr52a) and a straight path Tr52b outside (hereinafter referred to as the outside straight path Tr52b), as shown in FIG. 5A. These paths are set such that, in the inside straight path Tr52a, the endless belt 52 moves from upstream to downstream in the MD direction, and in the outside straight path Tr52b, the endless belt 52 moves in the opposite direction.

Further, the rotational axes C53 of all pulleys 53, 53, and 53D are along the Z direction, which is the thickness direction of the combined body 7G (that is, a direction perpendicular to both of the MD direction and CD direction). Therefore, in the inside straight path Tr52a, a substantially flat belt surface 52s of the endless belt 52 has a function as a wall. The wall is facing opposite to the bent section 7Gb of the combined body 7G or neighbouring portion thereof and extends straight along a direction parallel to the MD direction, as shown in FIG. 5C. The wall regulates shifting of the combined body 7G in the CD direction.

In this regards, in order for the wall to regulate definitely shifting of the combined body 7G in the CD direction, the space δ52 in the CD direction between the inside straight path Tr52a of the left shift-regulating guide member 50L and the inside straight path Tr52a the right shift-regulating guide member 50R (See FIG. 6A or 6C), that is, the space δ52 between the belt surface 52s of the left endless belt 52 and the belt surface 52s of the right endless belt 52 which are facing opposite to each other, are set such that the space is the same or within plus and minus 10 percent of the distance in the CD direction between the pair of bent sections 7Gb and 7Gb of the combined body 7G, in this example.

Incidentally, as mentioned above, during facing opposite to the bent section 7Gb of the combined body 7G or neighbouring portion thereof (hereinafter referred to as the bent section 7Gb, etc), the endless belt 52 moves along the MD direction in the same direction in which the combined body 7G is conveyed (See FIGS. 5A to 5C). Therefore, even if the foregoing bent section 7Gb, etc comes into contact with the belt surface 52s of the endless belt 52, a force to cease the conveying of the combined body 7G is less likely to be exerted because the endless belt 52 moves in the MD direction. This can moderate sliding resistance which may be caused considerably between the shift-regulating guide member and the combined body 7G if the shift-regulating guide member is a fixed wall which is immovable in the MD direction.

Further, in this example, as a power source of the drive pulley 53D which drives the endless belt 52, the same power source as the drive roller 23D of the suction belt conveyor 20 is used. That is, in the example of FIG. 6A, power-transmitting member (not shown) such as a spur gear, a bevel gear, etc are provided between a shaft 23s coaxially extending from one end section of the drive roller 23D and a shaft (not shown) of a rotational axis C53 of the drive pulley 53D. The rotating force is transmitted through the power-transmitting member from the drive roller 23D to the drive pulley 53D, which makes the drive pulley 53D driven and rotate. Therefore, the rate of rotation such as the gear ratio of the power-transmitting member etc can be set such that the moving speed of the endless belt 52 in the MD direction is the same or within plus and minus 10 percent of the conveying speed of the combined body 7G. This configuration can keep the sliding resistance between the endless belt 52 and the combined body 7G to the minimal. Therefore, such a setting is used in this example.

In this regards, in this example, the drive pulleys 53D and 53D of the left and right shift-regulating guide members 50L and 50R are connected to each other by a connecting shaft which is not shown and is along the CD direction. Thereby, the foregoing rotating force is transmitted to the endless belt 52 of the right shift-regulating guide member 50L through these drive pulleys 53D and 53D; as a result, the endless belt 52 of the right shift-regulating guide member 50R is driven and moves in synchronization with the endless belt 52 of the left shift-regulating guide member 50L.

Further, in the example of FIG. 6A, the inside straight paths Tr52a and Tr52a of the shift-regulating guide members 50L and 50R are provided throughout substantially total length of the installed area (for example, more than or equal to 90 percent of the installed area) of the folding guide members 40L and 40R in the MD direction. However, the invention is not limited thereto. Specifically speaking, a reasonable shift-regulating effect can be expected if the inside straight paths Tr52a and Tr52a are provided in at least part of the foregoing installed area in which the folding guide members 40L and 40R are arranged. However, it is preferable that the inside straight paths Tr52a and Tr52a are provided throughout substantially total length of the installed area as shown in FIG. 6A, because the position of the combined body 7G in the CD direction can stabilize definitely.

Further, in the same manner as the example of FIG. 6A, a starting position of forming the bent sections 7Gb and 7Gb, at which the rotational axes C30 of the standing guide members 30L and 30R are located, is located more upstream in the MD direction than the inside straight paths Tr52a and Tr52a of the shift-regulating guide members 50L and 50R. However, the invention is not limited thereto. That starting position may be located in the inside straight paths Tr52a and Tr52a. In this case, the bent sections 7Gb and 7Gb of the combined body 7G can be guided immediately after the bending by the shift-regulating guide members 50L and 50R; as a result, the position of the combined body 7G in the CD direction can stabilize.

Further, in the example of FIG. 6A, the pulleys 53 and 53 determine the straight path Tr52a related to the endless belt 52, and an additional pulley 53A is rotatably arranged between the pair of pulleys 53 and 53. The additional pulley 53A is for keeping straight the inside straight path Tr52a. Further, in order to guide the endless belt 52 along the inside straight path Tr52a, flat fixed guide plates 55 are arranged at positions between the pulleys 53, 53, and 53A adjacent to each other in the MD direction. The fixed guide plate 55 is along the MD direction and is installed slightly more outwardly in the CD direction than the inside straight path Tr52a.

Therefore, in the case where a part of the endless belt 52 expands outwardly in the CD direction due to a contact with the combined body 7G, the additional pulley 53A or the fixed guide plate 55 comes into contact with the endless belt 52 from outside the CD direction and regulates shifting of the endless belt 52 such that the endless belt 52 does not shift more outwardly. This keeps the endless belt 52 substantially straight along the MD direction. However, the additional pulley 53A and the fixed guide plate 55 are not necessary.

Incidentally, it is desirable that the belt surface 52s of the endless belt 52 of the shift-regulating guide member 50L has a function to suck and hold a thing. With such an endless belt 52, the endless belt 52 moves along the MD direction together with the combined body 7G as a substantially unitary body while the bent section 7Gb, etc of the combined body 7G are sucked and held by the belt surface 52s. This can prevent more effectively sliding resistance between the shift-regulating guide member 50L, which is the endless belt 52, and the combined body 7G. In this regards, the function of the belt surface 52s to suck and hold a thing is realized as follows. A plurality of suction holes (not shown) are formed on the belt surface 52s through the belt 52 in a thickness direction thereof. Opposite to these suction holes, an opening of a suction box, which includes a negative pressure chamber, is disposed. And, suction through the suction holes is realized by negative pressure of the negative pressure chamber. It should be noted that suction through the foregoing suction holes of the endless belt 22 of the suction belt conveyor 20 is realized in the same configuration as the foregoing suction box.

Further, in the foregoing configuration, the endless belt 52 of the shift-regulating guide member 50L is a driving belt. However, the invention is not limited thereto. For example, the endless belt 52 may be a driven belt which moves (gets turned) by being in contact with the bent section 7Gb, etc of the combined body 7G and thereby obtains a force to move in the MD direction from the combined body 7G. Comparing this case to the case in which the shift-regulating guide member is a fixed wall, this configuration also can reduce relatively sliding resistance between the endless belt 52 and the combined body 7G, as the endless belt 52 can be rotated along with the MD direction. However, the driving belt is more desirable because sliding resistance is greater than the foregoing case in which the shift-regulating guide member 50L is a driving belt.

Second Embodiment

FIGS. 7A to 7C are schematic explanatory diagrams of the folding apparatus 10a according to the second embodiment. FIG. 7A is a schematic top view of the folding apparatus 10a, FIG. 7B is a view taken along line B-B as viewed from the arrow side (side view) in FIG. 7A, and FIG. 7C is a view taken along line C-C as viewed from the arrow side in FIG. 7A. It should be noted that the combined body 7G is not shown in any of these figures.

In the foregoing first embodiment, the endless belt 52 is used as the shift-regulating guide member 50L (50R). A guide member 50La (50Ra) according to the second embodiment differs therefrom in that the guide rollers 58, 58, . . . (corresponding to roller member) are used.

That is, in the folding apparatus 10a, a plurality of guide rollers 58, 58, . . . are arranged at respective positions on the both sides of the conveying path Tr7G (that is, on the both left and right sides in the CD direction) and the guide rollers 58, 58 . . . are lined up straight at a predetermined arrangement interval P in the MD direction, as shown in FIG. 7A. Further, the rotational axes C58 of the guide rollers 58, 58, . . . are along in the Z direction. Therefore, the outer peripheral face of each of the guide rollers 58, 58, . . . faces the bent section 7Gb of the combined body 7G or neighbouring portion thereof, as shown in FIG. 7C. Furthermore, the guide rollers 58, 58, . . . are configured to be driven and rotated by obtaining the rotating force from a suitable power source.

Therefore, even if the bent section 7Gb, etc of the combined body 7G comes into contact with the outer peripheral face of the guide roller 58, a force to cease the conveying of the combined body 7G is less likely to be exerted because the guide roller 58 is driven and rotates. This can moderate sliding resistance which may be caused considerably between the guide member and the combined body 7G if the shift-regulating guide member is a fixed wall which is immovable in the MD direction.

Further, all guide rollers 58, 58, . . . , which belong to the left shift-regulating guide member 50La, are arranged such that the outer peripheral face of each of the guide rollers 58, 58, . . . touches a single straight line which is parallel to the MD direction. In addition thereto, all guide rollers 58, 58, . . . , which belong to the right shift-regulating guide member 50Ra, are arranged such that the outer peripheral face of each of the guide rollers 58, 58, . . . touches a single straight line which is parallel to the MD direction.

Therefore, the bent section 7Gb, etc of the combined body 7G do not get stuck to the outer peripheral face of each of the guide rollers 58, 58, . . . . As a result, the guide rollers 58, 58, . . . can guide smoothly those bent section 7Gb, etc in the MD direction.

In this regards, an electric motor, etc can be provided as a example of power source of the guide rollers 58, 58, . . . . Further, that power source may be disposed of each of the guide rollers 58. Depending on cases, it is preferable that the plurality of guide rollers 58, 58, . . . are connected to a single power source, using a suitable power-transmitting member such as a gear, a pulley, and a timing belt, etc, and thereby the plurality of guide rollers 58, 58, . . . are driven and rotated simultaneously. Further, the circumferential speed of the outer peripheral face of the guide rollers 58, 58, . . . is preferably set to be the same or within plus and minus 10 percent of the conveying speed of the combined body 7G. This configuration can keep the sliding resistance between each of the guide rollers 58, 58, . . . and the combined body 7G to the minimal.

Further, it is desirable that the arrangement interval P58 of the guide rollers 58, 58, . . . in the MD direction is smaller than the placement interval P1 of the napkins 1, 1, . . . in the combined body 7G (FIG. 4). This enables the napkin 1 to smoothly transfer from a predetermined guide roller 58 to the next guide roller 58 adjacent downstream thereof.

Incidentally, in the foregoing second embodiment, the guide rollers 58, 58, . . . are drive rollers. However, the invention is not limited thereto. For example, the guide rollers 58, 58, . . . may be follower rollers which gets turned by being in contact with bent section 7Gb of the combined body 7G or neighbouring portion thereof and thereby obtains a force to move in the MD direction from the combined body 7G. Comparing this case to the case in which the shift-regulating guide member is a fixed wall, this configuration also can reduce relatively sliding resistance between the guide roller 58 and the combined body 7G, as the guide roller 58 can be moved and rotated (get turned) along the MD direction. However, the drive roller is more desirable because sliding resistance is greater than the foregoing case in which the shift-regulating guide member 50La and 50Ra are drive rollers.

Other Embodiments

The embodiments according to the invention has been described above. However, the invention is not limited to these embodiments, and modifications described below are possible.

In the foregoing embodiment, the example of the sanitary napkin 1 is provided in which the absorbent article absorbs menstrual blood which is an example of bodily fluid. However, the invention is not limited thereto. For example, a disposable diaper to absorb urine, which is an example of bodily fluid (including exudates), or a pet pad to absorb urine of a pet etc may be employed.

In the foregoing embodiment, the wrapping sheet 7a is provided as an example of the continuous sheet 7, and the napkin 1 is provided as an example of an object which is placed on the continuous sheet 7. However, the invention is not limited thereto. For example, a disposable diaper or pet pad, etc may be employed as an object. Further the continuous sheet 7 may be a component of the absorbent article in the finished product. Furthermore, the continuous sheet 7 is not limited to the foregoing nonwoven fabric, and may be woven fabric or film.

In the foregoing embodiment, the combined body 7G is folded in three. In other words, the combined body 7G is folded such that the one end section 7GR in the CD direction covers and overlaps the other end section 7GL. However, the invention is not limited thereto. More specifically, the end sections 7GL and 7GR may be respectively folded in two such that a space in the CD direction exists between the one end section 7GR and the other end section 7GL. Also, only either one of the end sections 7GL and 7GR may be folded.

In the foregoing embodiment, the MD direction is parallel to the horizontal direction. However, the invention is not limited thereto. The MD direction may be inclined at a certain angle with respect to the horizontal direction.

In the foregoing embodiment, the suction belt conveyor 20 is provided as an example of the conveying apparatus which conveys the combined body 7G in the MD direction. However, the invention is not limited thereto. For example, a roller conveyor may be employed. It should be noted that the roller conveyor is an apparatus composed of a plurality of conveying rollers which rotate about the rotational axis in the CD direction, lined up at a proper interval in the MD direction. Some or all of the conveying rollers are drive rollers which are driven and rotated by obtaining the rotating force from a power source such as an electric motor, etc, and the rollers except the drive rollers are follower rollers which are moved and rotated by obtaining the rotating force from the contact with the combined body 7G which is being conveyed.

In the foregoing first embodiment, a rubber belt etc is provided as an example of the endless belt 52 of the shift-regulating guide member 50L(50R). However, the material is not limited to a rubber-based material as long as the material has suitable flexibility. For example, guide members made of resin or metal may be employed. Further, in the foregoing description, the belt surface 52s is substantially flat. However, the invention is not limited thereto. The belt surface 52s may include projections and depressions, and also may include a plurality of through holes formed thereon.

In the foregoing embodiment, the case in which the left folding guide member 40L and the right folding guide member 40R are arranged overlapping each other along the MD direction is provided as an example. In the description, it is also mentioned that a configuration without overlapping may be employed. An example of the configuration without overlapping shown in the schematic top view in FIG. 8 may be employed.

It should be noted that, in this configuration, folding of the left end section 7GL and folding of the right end section 7GR are done completely in sequence as follows: the left end section 7GL of the combined body 7G is stood and laid completely on the combined body 7G, and thereafter the right end section 7GR of the combined body 7G is stood and laid on the combined body 7G. In other words, folding operation of the left end section 7GL and the right end section 7GR are not performed in the least simultaneously.

The detailed description will be made below. Firstly, in this example, the conveying path Tr7G of the combined body 7G is divided into two parts along the MD direction, the conveying path Tr7G being formed along the MD direction by the suction belt conveyor 20. That is, the conveying path Tr7G is divided into an upstream conveying path Tr7Gu and a downstream conveying path Tr7Gd located downstream thereof. In the upstream conveying path Tr7Gu, the left end section 7GL of the combined body 7G is folded, and in the downstream conveying path Tr7Gd, the right end section 7GR of the combined body 7G is folded.

As shown in FIG. 8, the standing guide member 30L is provided at the upstream end in the upstream conveying path Tr7Gu. Only single circular plate member 30L, which serves as the standing guide member 30L, is provided for the left end section 7GL of the combined body 7G. When the combined body 7G (not shown in FIG. 8) passes the position of the circular plate member 30L, only the left end section 7GL of the combined body 7G is stood by the circular plate member 30L, and the right end section 7GR is not stood.

Further, the left guide member 40L, which serves as the folding guide member 40L, is arranged downstream than the standing guide member 30L in the upstream conveying path Tr7Gu. Therefore, when the combined body 7G passes this position, the stood left end section 7GL is laid on the combined body 7G and is folded.

It should be noted that the shift-regulating guide member 50 is provided only on the left side in the upstream conveying path Tr7Gu, and is not provided on the right side. This is because the shift-regulating guide member has a function to regulate shifting of the combined body 7G in the CD direction by being in contact with the bent section 7Gb, etc of the combined body 7G, but at this point the bent section 7Gb, etc do not exist on the right side of the combined body 7G. Therefore, the shift-regulating guide member 50 is not provided on the right side of the upstream conveying path Tr7Gu. Further, in the figures, the endless belt 52 having the same configuration as the first embodiment is provided as the shift-regulating guide member 50. Instead of the endless belt 52, the guide rollers 58, 58, ... according to the second embodiment may be provided.

After the combined body 7G has finished passing the upstream conveying path Tr7Gu, and the combined body 7G passes the downstream conveying path Tr7Gd. At the upstream end in the downstream conveying path Tr7Gd, only single circular plate member 30R, which serves as the standing guide member 30R, is provided for the right end section 7GR of the combined body 7G. When the combined body 7G passes the position of the circular plate member 30R, the right end section 7GR of the combined body 7G is stood by the circular plate member 30R.

Further, the right guide member 40R, which serves as the folding guide member 40R, is arranged downstream than the standing guide member 30R in the downstream conveying path Tr7Gd. Therefore, when the combined body 7G passes this position, the stood right end section 7GR is laid on the combined body 7G and is folded.

It should be noted that the shift-regulating guide members 50 and 50 are provided on the both left and right sides in the downstream conveying path Tr7Gd. This is because while those shift-regulating guide members 50 and 50 have a function to lay the right end section 7GR of the combined body 7G in the downstream conveying path Tr7Gd, the left end section 7GL has already been folded and so the bent sections 7Gb and 7Gb etc exist on the both left and right sides. Further, in the figures, the endless belts 52 and 52 are provided as the shift-regulating guide members 50 and 50. Instead of those endless belts 52 and 52, the guide rollers 58, 58, ... according to the second embodiment may be provided in similar to the foregoing.

REFERENCE SIGNS LIST 1 sanitary napkin (absorbent article), 1w wing, 2 top sheet, 3 absorbent body, 4 back sheet, 5a adhesive, 5b adhesive, 6a protection sheet, 6b protection sheet, 7 continuous sheet, 7a wrapping sheet, 7G combined body 7GC central section, 7GL left end section, 7GLb portion, 7GLe portion, 7GR right end section, 7Gb bent section, 7L end section, 7Lg long edge, 7R end section, 7S short edge, 7j sealed section, 8 tape, 10 folding apparatus, 10a folding apparatus, 20 suction belt conveyor, 22 endless belt, 22s belt surface, 23 roller, 23D drive roller, 23s shaft, 30L circular plate member (standing guide member), 30R circular plate member (standing guide member), 31 shaft member, 40L flat plate member (folding guide member), 40Lsr right edge, 40Ld downstream end, 40R flat plate member (folding guide member), 40Rs1 left edge, 40Ru upstream end, 42 support roll, 50 shift-regulating guide member, 50L shift-regulating guide member, 50La shift-regulating guide member, 50R shift-regulating guide member, 50Ra shift-regulating guide member, 52 endless belt (belt member), 52s belt surface, 53 pulley, 53A additional pulley, 53D drive pulley, 55 fixed guide plate, 58 guide roller (roller member), C23 rotational axis, C30 rotational axis, C53 rotational axis, C58 rotational axis, Tr7G conveying path, ED downstream end, EU upstream end, Tr7Gd downstream conveying path, Tr7Gu upstream coveying path, Tr22 path, Tr22d straight path, Tr22u straight path, Tr52 path, Tr52a insider straight path, Tr52b outside straight path

The invention claimed is:

1. A folding apparatus for a combined body of a continuous sheet related to an absorbent article, that folds at least one end section of the continuous sheet on one side in a width direction together with one end section of an object in the width direction while conveying the combined body in a conveying direction, the combined body being formed by placing intermittently a plurality of the objects on the continuous sheet at a predetermined interval, the conveying direction being a direction in which the continuous sheet continues, comprising:
   a standing guide member that is disposed at a predetermined position in the conveying direction, and that stands the one end section of the combined body in the width direction by bending a predetermined section of the combined body in the width direction and forming a bent section;
   a folding guide member that is disposed at a predetermined position in the conveying direction to correspond to the stood one end section and that folds the stood one end section by laying the one end section towards a section that is located closer to another side than the one end section in the combined body; and
   a shift-regulating guide member that regulates shifting of the combined body towards the one side in the width direction by coming into contact, from the one side, with the combined body when laying the one end section towards the section that is located closer to the other side, wherein
   the shift-regulating guide member is a belt member,
   the belt member is an endless belt that moves along a predetermined path by obtaining from a power source a necessary force to move, and
   in a predetermined range of the path, the endless belt moves along the conveying direction in conjunction with the conveying of the combined body while a belt surface thereof is facing the bent section.

2. A folding apparatus for a combined body of a continuous sheet related to an absorbent article according to claim 1, wherein
   the endless belt includes a plurality of suction holes on the belt surface, and
   the belt surface sucks and holds the bent section by suction through the suction holes.

3. A folding apparatus for a combined body of a continuous sheet related to an absorbent article according to claim 1, wherein
   the folding apparatus further includes a conveying belt that includes a plurality of suction holes on a belt surface thereof and moves along the conveying direction, and
   the combined body is conveyed by the conveying belt in the conveying direction while the belt surface is sucking and holding a central section of one surface of the continuous sheet by suction through the suction holes.

4. A folding apparatus for a combined body of a continuous sheet related to an absorbent article according to claim 1, wherein
   the standing guide members are disposed on respectively both end sections of the combined body in the width direction to correspond respectively to the both end sections,
   the folding guide members are disposed on respectively both end sections of the combined body in the width direction to correspond respectively to the both end sections, and the shift-regulating guide members are disposed on respectively both end sections of the combined body in the width direction to correspond respectively to the both end sections.

5. A folding apparatus for a combined body of a continuous sheet related to an absorbent article, that folds at least one end section of the continuous sheet on one side in a width direction together with one end section of an object in the width direction while conveying the combined body in a conveying direction, the combined body being formed by placing intermittently a plurality of the objects on the continuous sheet at a predetermined interval, the conveying direction being a direction in which the continuous sheet continues, comprising:
- a standing guide member that is disposed at a predetermined position in the conveying direction, and that stands the one end section of the combined body in the width direction by bending a predetermined section of the combined body in the width direction and forming a bent section;
- a folding guide member that is disposed at a predetermined position in the conveying direction to correspond to the stood one end section and that folds the stood one end section by laying the one end section towards a section that is located closer to another side than the one end section in the combined body; and
- a shift-regulating guide member that regulates shifting of the combined body towards the one side in the width direction by coming into contact, from the one side, with the combined body when laying the one end section towards the section that is located closer to the other side, wherein
the shift-regulating guide member is a roller member that rotates along the conveying direction,
the roller member is a drive roller that is driven and rotates about a predetermined rotational axis,
the drive roller is driven and rotates in conjunction with the conveying of the combined body while an outer peripheral face thereof is facing the bent section.

6. A folding apparatus for a combined body of a continuous sheet related to an absorbent article according to claim 5, wherein
- a plurality of the roller members are arranged at a predetermined arrangement interval in the conveying direction, and
- the arrangement interval is smaller than the predetermined interval related to the objects.

7. A folding method for a combined body of a continuous sheet related to an absorbent article, that folds at least one end section of the continuous sheet on one side in a width direction together with one end section of an object in the width direction while conveying the combined body in a conveying direction, the combined body being formed by placing intermittently a plurality of the objects on the continuous sheet at a predetermined interval, the conveying direction being a direction in which the continuous sheet continues, comprising:
standing the one end section of the combined body in the width direction by bending a predetermined section of the combined body in the width direction and forming a bent section, using a standing guide member that is disposed at a predetermined position in the conveying direction;
folding the stood one end section by laying the one end section towards a section that is located closer to another side than the one end section in the combined body, using a folding guide member that is disposed at a predetermined position in the conveying direction to correspond to the stood one end section; and
regulating shifting of the combined body towards the one side in the width direction by bringing a shift-regulating guide member into contact, from the one side, with the combined body when laying the one end section towards the section that is located closer to the other side, wherein
the shift-regulating guide member is a belt member,
the belt member is an endless belt that moves along a predetermined path by obtaining from a power source a necessary force to move, and
in a predetermined range of the path, the endless belt moves along the conveying direction in conjunction with the conveying of the combined body while a belt surface thereof is facing the bent section.

8. A folding method for a combined body of a continuous sheet related to an absorbent article, that folds at least one end section of the continuous sheet on one side in a width direction together with one end section of an object in the width direction while conveying the combined body in a conveying direction, the combined body being formed by placing intermittently a plurality of the objects on the continuous sheet at a predetermined interval, the conveying direction being a direction in which the continuous sheet continues, comprising:
standing the one end section of the combined body in the width direction by bending a predetermined section of the combined body in the width direction and forming a bent section, using a standing guide member that is disposed at a predetermined position in the conveying direction;
folding the stood one end section by laying the one end section towards a section that is located closer to another side than the one end section in the combined body, using a folding guide member that is disposed at a predetermined position in the conveying direction to correspond to the stood one end section; and
regulating shifting of the combined body towards the one side in the width direction by bringing a shift-regulating guide member into contact, from the one side, with the combined body when laying the one end section towards the section that is located closer to the other side, wherein
the shift-regulating guide member is a roller member that rotates along the conveying direction,
the roller member is a drive roller that is driven and rotates about a predetermined rotational axis, and
the drive roller is driven and rotates in conjunction with the conveying of the combined body while an outer peripheral face thereof is facing the bent section.

* * * * *